United States Patent
Bert et al.

(10) Patent No.: US 9,044,599 B2
(45) Date of Patent: Jun. 2, 2015

(54) DEPOSITION OF AN INTENDED DOSE DISTRIBUTION IN A CYCLICALLY MOVED TARGET AREA

(75) Inventors: Christoph Bert, Aschaffenburg (DE); Eike Rietzel, Weiterstadt (DE)

(73) Assignee: GSI Helmholtzzentrum für Schwerionenforschung GmbH, Darmstadt (DE)

( * ) Notice: Subject to any disclaimer, the term of this patent is extended or adjusted under 35 U.S.C. 154(b) by 1180 days.

(21) Appl. No.: 12/996,700

(22) PCT Filed: Jun. 8, 2009

(86) PCT No.: PCT/EP2009/004096
§ 371 (c)(1),
(2), (4) Date: Apr. 22, 2011

(87) PCT Pub. No.: WO2009/149882
PCT Pub. Date: Dec. 17, 2009

(65) Prior Publication Data
US 2011/0297849 A1    Dec. 8, 2011

(30) Foreign Application Priority Data

Jun. 9, 2008 (DE) .......................... 10 2008 027 485

(51) Int. Cl.
*A61N 5/01* (2006.01)
*A61N 5/10* (2006.01)

(52) U.S. Cl.
CPC ................ *A61N 5/10* (2013.01); *A61N 5/1043* (2013.01); *A61N 5/1065* (2013.01); *A61N 2005/1087* (2013.01); *A61N 5/1044* (2013.01)

(58) Field of Classification Search
CPC ....................... A61N 5/01; A61N 5/10; A61N 5/103–5/1084; A61N 2005/1071–2005/1072
USPC ....................... 600/1–8; 250/396 R–396 ML, 250/423 R–423 F, 491.1–492.3, 250/493.1–504 H; 378/65
See application file for complete search history.

(56) References Cited

U.S. PATENT DOCUMENTS 6,614,038 B1 * 9/2003 Brand et al. ............... 250/492.3
(Continued)

FOREIGN PATENT DOCUMENTS

DE    10 2005 058 207    10/2006
(Continued)

OTHER PUBLICATIONS

Grozinger, SO. Volume Conformal Irradiation of Moving Target Volumes with Scanned Ion Beams. Doctoral Dissertation. Technischen Universitat Darmstadt, 2004.*
(Continued)

*Primary Examiner* — Catherine B Kuhlman
(74) *Attorney, Agent, or Firm* — Reising Ethington PC (57) ABSTRACT

The invention concerns a process for the deposition of an intended dose distribution in a cyclically moved target region moving cyclically (102) by means of multiple irradiations with a beam (105) approaching matrix points of a target matrix in at least two scannings, wherein in each of the scannings, matrix points are approached sequentially. It is characterized through the steps: establishing the maximal tolerance level for local deviation from the intended dose distribution, de-synchronizing the sequence of the irradiation and the cyclical motion of the target region (102), and partitioning the irradiation of the target region (102) in a sufficient number of scannings such that local deviations from the intended dose distribution correspond at most to the maximal tolerance level of deviation from the intended dose distribution. Furthermore, the invention also concerns an irradiation apparatus for executing a process of this type and a process for determining the control parameters for said irradiation apparatus.

32 Claims, 4 Drawing Sheets

(56) References Cited

U.S. PATENT DOCUMENTS

| | | | |
|---|---|---|---|
| 2004/0002641 A1* | 1/2004 | Sjogren et al. | 600/407 |
| 2008/0023644 A1* | 1/2008 | Pedroni | 250/400 |
| 2008/0067401 A1* | 3/2008 | Harada | 250/396 R |

FOREIGN PATENT DOCUMENTS

| | | |
|---|---|---|
| JP | 2006087649 | 4/2006 |
| WO | WO 00/48680 | 8/2000 |
| EP | 1905481 | 4/2008 |

OTHER PUBLICATIONS

Christoph Bert "Bestrahlungsplanung fur bewegte zielvolumina in der Tumortherapie mit gescanntem Kohlenstoffstrahl" Internet Citation [online] Feb. 3, 2006 XP002481370.

M.H. Phillips, et al "Effects of respiratory motion on dose uniformity with a charged particle scanning method" Physics in Medicine and Biology,Taylor & Francis Ltd, Jan. 1992.

Christoph Bert & Eike Rietzel "4D Treatment planning for scanned ion beams" Radiation Oncology, BioMed Central 2007 doc;10.1186/1748-717X224, 2:24 Pub date Jul. 3, 2007.

Shinichiro Mori "Respiratory correlated segment reconstruction algorithum towards four-dimensional radiation therapy using carbon ion beams" Radio&Oncology 80(2006)341-348.

* cited by examiner

Irradiation planning:

| Irradiation plan creation/optimization |

↓

| Establishment of the irradiation pathway and layered or volumetric irradiation |

Prior to the irradiation: ↓

| Determination of the breathing cycle |

↓

| Adjustment of the beam velocity |

↓

| Establishment of the number of scans per layer |

During the irradiation: ↓

| Measurement of the breathing trajectory; if applicable the number of and/or the initiation points of the scans; if applicable the random time delays between scans |

↓

| Audio and/or visual feedback |

Fig. 4

Measures for de-synchronization:

- Distribution of the scans over a minimum time period
- Halting of the irradiation during resting phases of the motion
- Execution of the irradiation during resting phases of the motion
- Modification of the pathway from one scan to another
- Influence to the motion sequence with the aid of a communication device
- Initiation of scanning after random time delay
- Initiation of layers after random time delay
- Modification of the pathway from layer to layer
- Modification of the beam intensity
- Modification of the sequence of irradiation from one session to another

DEPOSITION OF AN INTENDED DOSE DISTRIBUTION IN A CYCLICALLY MOVED TARGET AREA

The present invention relates to a process and a device for the deposition of a an intended dose distribution in a cyclically moved target region by means of multiple irradiations with a beam approaching matrix points as well as a process for determining the control parameters for the device.

The irradiation of a target region with a beam approaching various points (beam scanning) is known per se. This is used for example in the particle irradiation of tumors, in particular with protons, α-particles and carbon nuclei. Portions of the target region are scanned sequentially with the beam (scanning).

Particle beams of this type are particularly advantageous for the scanning of three-dimensional target regions, as they pass through a maximum energy deposition level towards their end (Bragg Peak). This allows for example, for embedded three-dimensional structures to be effectively irradiated without damaging the embedding surroundings too much. Frequently, three-dimensional target regions are irradiated in layers, whereby the specific beam energy determining the penetrating depth is selected at a constant level for each respective layer (isoenergy layer). As a matter of principle the invention also concerns embodiments with which the beam is generated by means of electromagnetic waves. In addition, the invention is also concerned, in principle, with embodiments for irradiating a two-dimensional target region.

The beam normally has a smaller cross-section than the target region. In order to irradiate the entire target region, the beam approaches numerous matrix points sequentially. The sequentially irradiated matrix points are also referred to as the pathway (scan path). If an overlap of the target matrix and the target region comprises the entire target region, then through successive scans of the matrix points the target region can be irradiated entirely. In this regard, a subdivision of the target region into numerous matrix points is also refereed to.

The measures described may be applied to a variety of scanning procedures.

With the so-called spot scan procedure, the particle beam is aimed at each matrix point for a predetermined time period and/or deposits a predetermined number of particles at each matrix point and is then turned off while deflection magnets etc. are adjusted for the next matrix point.

With the so-called raster scan procedure, the particle beam is aimed at each matrix point for a predetermined time period or deposits a predetermined number of particles at each matrix point, but is not, or not always, turned off between the matrix points.

With so-called continuous scanning procedures, the matrix points form interconnected lines, thereby forming continuous (or semi-continuous) quantities, whereby the number of said lines can be basically countable infinite. The particle beam in a continuous scan procedure, at least within one line or row, respectively, in an isoenergy layer is continuously deflected and scans the matrix points without stopping at individual locations.

A continuous scanning procedure can also be executed with a depth modulation device, with which the penetration depth of the particle beam is continuously modulated.

The pathway can run basically within an isoenergy layer, whereby the beam is only deflected in its beam direction, i.e. laterally, or it can also run basically between isoenergy layers whereby the energy of the beam is altered.

Normally, as with the irradiation of tumors, a specific distribution of the dose, i.e. an intended dose distribution, to the target region should be obtained. The intended dose distribution is quantified as deposited energy per surface unit, or respectively, per volume unit. Conventionally, the amount of a dose is given in Joules/kilogram (Gray).

With the equally known multiple irradiation procedure using a beam which targets a variety of points (rescanning), the intended dose in a single session is applied through multiple scans, which, as the case may be, may be separated by short breaks. Within the individual scans numerous matrix points, although not necessarily all, are irradiated in sequence. In the course of a session, normally a majority of the matrix points, or all of the matrix points, and thereby a majority of the target region, or the entire target region, is irradiated several times. The entire dose which is to be applied in the session for each matrix point is distributed between the individual scans, and this either equally, or as the case may be, with differing weighting.

Frequently the target regions to be irradiated do not move in relation to the irradiating device. The irradiation of a cyclically moved target region is also known however, for example, a tumor moving due to respiration or due to another organ motion of a person.

Cyclical motions comprise, basically, periodic motion and semi-periodic motion deviating from mathematically exact periodicity. In particular, such motions which occasionally rest in a phase are considered cyclical.

The present invention has the objective of providing an advantageous process and an advantageous apparatus for the deposition of an intended dose distribution in a cyclically moved target region, by means of multiple irradiations with a matrix point approaching beam, as well as a process for determining the control parameters of the apparatus.

This objective is achieved through processes for the deposition of an intended dose distribution in a cyclically moved target region by means of multiple irradiations with a beam approaching matrix points of a target matrix in at least two scans, whereby in each scan matrix points are scanned sequentially. It is characterized by the steps: establishing a maximal tolerance level of a local deviation from the intended dose distribution, de-synchronization of the sequence of the irradiation and the cyclical motion of the target region, and partitioning of the irradiation of the target region in a sufficient number of scans such that local deviations from the intended dose distribution correspond to the maximal tolerance level of the deviation from the intended dose distribution.

Preferred embodiments of the invention are given in the dependent claims and shall be explained in greater detail in the following.

The invention is based on the observation that with cyclically moved target regions, the obtained dose distribution may deviate from the intended dose distribution; in particular, local overdosing and underdosing may occur.

The invention is based on the idea that the temporal sequence of the irradiation, in particular the approaching of the matrix points, and the cyclical motion may interact in such a manner that these local dose errors may occur. In other words: local deviations from the intended dose distribution may occur, or respectively, be intensified as a result of interference, or respectively, synchronization between the sequence of the irradiation and the cyclical motion of the target region.

As an example, the pathway of the beam may temporarily run parallel to the moving target region, resulting in an overdosing, or at other times in the opposite direction, resulting in underdosing.

Furthermore, as a result of an unfavorable synchronization between the sequence of the scans and the cyclical motion, local deviations from the intended dose distribution may be increased from scan to scan. In this case it is also possible to speak of a synchronization of two movements. Regarding the term "synchronization" as it is used above, this may also refer to a temporal sequence in the sense of a repetition of an erroneous dosage in different scans of the same location, or respectively, the same region of the target region.

The invention takes as a basis the idea that through a de-synchronization, one may also use the term de-coupling, of the sequence of irradiation and the sequence of cyclical motion, deviations from the intended dose can be kept to a minimum. As a result of de-synchronization, the occurrence of synchronization is impaired or even avoided; by this means it is possible to keep local dose errors at a relative minimum with statistical means applied to the scans or by the means of selected counteractions.

In other words: The sequence of the multiple irradiations and the cyclical motion are coordinated to each other according to the invention, or respectively, de-synchronized, such that they counteract dose errors, or respectively, a dose error occurring in one of the scans will only have a weak, if any, effect on the obtained dose distribution.

First, the maximal tolerance level for the deviation from the intended dose distribution is determined. This may be different from one application to another and is determined empirically or based on model calculations (see below); the corresponding data can be stored in a table in the memory bank of a controller computer (see below). Particularly in treating patients, consideration of the intended dose can also represent the biologically effective dose. It is not necessary to enter the deviation tolerance level again for each irradiation. The data need not specifically be given quantitatively; it is basically sufficient if the process is designed such, or respectively, certain parameters are selected such, that the deviations from the intended dose are smaller than, for example, in previous cases, empirical studies, reference cases or in model calculations; the determination may, thereby, be carried out based on the definite form of the process as well. In other words: the "determination" can also be established by the "design" of the irradiation apparatus such that it falls below a maximal tolerance level of error. Preferably, local deviations from the intended dose distributions amount to a maximum of 30%. Increasingly preferable are the cases where the deviations have a maximum of 20%, 10%, 5%, or even only 2% in the order listed. Basically, it is also possible to determine the dose error online, in order to adjust the parameters of the irradiation procedure during irradiation.

A de-synchronization of the sequence of the multiple irradiations and the cyclical motion can be obtained through various measures. Such measures can basically be based on an adjustment and/or modification of the following values:

Number of scans (rescans);
Beam intensity, and related to it, the scanning rate;
Temporal distribution of the scans, e.g., in terms of the initiation of the respective scans;
In the case of three-dimensional target volumes the temporal distribution of the irradiation of layers, or respectively, of certain volumes within the individual scans, basically in respect to the initiation of the irradiation of a layer, or respectively, a volume, through varying the extraction from the accelerator or through passive energy modulation;
Initiation phase and/or cycle duration of the cyclical motion, insofar as the motion can be influenced;
Pathway of the beam in the target region, in particular within layers, or respectively, volumes within a respectively subdivided target region.

The irradiation is subdivided into as many scans as that local deviations from the intended dose distribution correspond at most to the deviations given above. As a basic principle, an increase in the number of scans means that, an erroneous amount of dose, in a single scan is less effective in relation to the total dosage distribution. Dose errors in single scans can cancel each other out, or respectively, compensate for each other.

Depending on the application in respect to the target which is to be irradiated, it is possible to carry out tests or model calculations in advance in order to determine the sufficient number of scans. Tests of this nature are normally carried out on so-called phantoms, based on a body made of Plexiglas or water; the results taken from tests on a phantom allow for conclusions to be drawn regarding irradiation parameters which are to be applied to other targets, in particular the number of scans. Where applicable, model calculations can also be carried out for individual patients or for groups of patients.

With the aid of the invention it is also possible to come to a better understanding of the interaction between a beam approaching matrix points and a cyclical motion of the target, which can contribute to an improvement of procedures and apparatuses used for multiple irradiations of this type; in particular, the parameters used for the multiple irradiations can also be checked or adjusted. Aside from the treatment of human beings or animals, the irradiation of organic material on the whole, particularly cells, or the irradiation of inorganic material such as plastics, is also relevant. In this manner, the invention can also aid in research regarding, for example, material characteristics; the above mentioned phantoms, for example, can be examined and improved. Through the use of such phantoms, and, as the case would be, embedded detectors, the opportunity to check or establish irradiation parameters is an obvious advantage.

In a preferred embodiment of the process according to the invention, at least one characteristic of the multiple irradiations is dependent on at least one characteristic of the cyclical motion. For example, the parameters determining the multiple irradiations can be adjusted for the properties, which characterize the cyclical motion. In this manner, it is possible for basically one property of the motion of an organ, e.g., the motion of the lungs and surrounding organs in a person resulting from breathing, to be translated into a signal and to be fed to a control device for controlling the multiple irradiations. As an example, the multiple irradiations can depend on the average cycle duration or the average amplitude of the motion.

It makes sense to make the following properties, or respectively, parameters of the multiple irradiations, dependent on at least one of the properties of the cyclical motion:

Number of scans in a session;
Beam intensity during a scan;
Rate at which the beam changes from one matrix point to another within a scan (one also refers to this as the beam velocity);
Initiation point in time of the individual scans.

The characteristics of the irradiation can basically be adjusted to the cycle period or the momentary phase.

The initiation point in time of the individual scans can be distributed
over a specific section of the cyclical motion, for example in a breathing motion, in a section of the inhalation or a section of the exhalation, over an entire cycle, such as a breathing cycle and over a time period which is larger than the length of a cycle.

They may, for example be selected such that one irradiation in particular, or more often, is carried out when the object being irradiated is in a state wherein the cyclical motion is either more or less strongly pronounced than in another state (see below).

This state of the target which is to be irradiated, or respectively, a property of the cyclical motion, can furthermore be translated into a signal which can be used to adjust, e.g., the starting point for individual scans. In this case, these starting points may be distributed either at regular intervals or randomly.

The signal may be determined repeatedly or progressively during the cyclical motion (online). The signal may however be monitored and/or determined in the framework of a planning phase prior to the actual treatment and derived thereby from a specific motion, such as a patient specific organ motion.

It is however also possible to establish a signal in advance which also has an influence on the cyclical motion (instruction signal). In this manner, for example, a person who is to be irradiated may be instructed by the signal to maintain a constant breathing cycle, or to make a change in the breathing cycle. In this manner, it is possible to tell the person when to inhale and when to exhale. In this case, the selection of the characteristics of the irradiation is dependent on the signal and thereby indirectly on the characteristics of the cyclical motion.

Preferably, during the multiple irradiations one of the parameters determining the multiple irradiations is modified. This can take place at regular intervals; preferably this occurs at random intervals.

The beam velocity and/or beam intensity used during a scan can be modified. Furthermore, breaks between individual scans may be varied, or the pathway of the beam during a session of multiple irradiations may also be varied.

A modification of this type can, for example, take place from one scan to another during an irradiation session or with an irradiation having multiple sessions from one session to another; in the latter case, the deposited radiation dose and the number of scans per session, in particular, can be modified. It is preferable that the modification takes place during the session.

Preferably, at least a portion of the matrix points is approached in different scans in different phases of the cyclical motion on purpose. This can be accomplished basically through the targeted initiation of different scans purposeful in different phases of the cyclical motion. An erroneous dose occurring in one of the phases is thus at least partially corrected through irradiation in the other phases. Particularly preferred is the case where at least 50%, better is 80% and in the best case 90% of the scans are initiated in different phases of the cyclical motion. Preferably, the cyclical motion is also monitored, in particular the motion cycle or phase is determined a number of times, or continuously.

Periodic motion refers to a definite cycle duration, abbreviated "cycle". With semi-periodic motions, at least an approximate cycle can be established, basically an average cycle from numerous cycles, or a typical cycle. If a cyclical motion deviates from a periodic motion as a result of, for instance, motionless moments, then one can at least temporarily assign an approximate cycle to these motions by evaluating certain time segments.

To determine a cycle, it is possible to base this on a system specific or person specific time. In this manner, the breathing cycle of an adult human being at rest is typically about four seconds. It is also possible however to fall back on an average cycle measured over numerous cycles. In a preferred embodiment, values greater than 100%, such as 140% for example, of the average measured, or empirical, or person specific, cycle is used.

In a preferred embodiment, the cycle prior to and/or during an irradiation, if applicable, approximately, is determined and at least a portion of the scans are distributed over a period of time that corresponds to between 50% and 140%, better, between 75% and 140% of the determined cycle. Other time periods of greater than 50%, or respectively, 75% can be advantageous; also, time periods of up to 100%. Preferably all scans are distributed over the specified time interval, or respectively, the selected time interval. A distribution over at least two cycles or over another selectable, if applicable, longer time period may be advantageous.

In this manner a distribution over various phases can be obtained. In particular, it is preferable that the scans are distributed as evenly as possible over the given time periods. The scans can however also be distributed randomly. Two important parameters which determine the distribution of the scans over the time period are the number of scans and the initiation point in time of the scans. In particular it is preferable, as already stated, that the initiation points in time of the scans are distributed either at regular intervals or randomly over the time period.

With a distribution of the scans over a minimum time period the execution of all of the scans, for example, occurring in a semi-static state of movement is avoided, which could have a negative effect on the statistical averaging of the motion.

It is preferable that the motion cycle prior to the initiation of the irradiation is determined. This is technically particularly simple. Preferably, measures are used thereby as well in order to maintain the cycle of the cyclical motion during irradiation at a nearly constant rate. If, for example, a person is treated, said person can attempt to maintain their breathing at a constant rate. The success of such efforts can be improved by means of preparatory measures, such as so-called "breath coaching" or training. In addition, the patient can be provided with a design trajectory by means, for example of a monitor.

Alternatively, or additionally, the cycle can be determined by means of monitoring the motion during irradiation, preferably numerous times, or continuously. In this manner, irradiation parameters, such as the number or initiation points in time of the scans can be adjusted during the irradiation modifying cycle. Preferably the cycle is continuously monitored and determined, which allows for a quick adjustment of the irradiation parameters.

As an example, it is possible to focus on the rising and falling of the rib cage when monitoring the breathing motion of a person, something that is easily accomplished on a technical level. It is also possible to measure the motion of the target region directly, e.g. through X-rays images taken continuously, or respectively, at time intervals, or through similar recording procedures which are able to capture internal movement.

It is basically advantageous as well to project the future motion based on the determined cycle, or respectively, the observed motion; in this manner, irradiation parameters can be adjusted for the future as well.

In order to ensure that the scans of the multiple irradiations are initiated at different phases of the cyclical motion, the cyclical motion, as presented above, can be monitored. It is preferable to stop the irradiation if the motion ceases for more than 50% of the motion cycle, because when the motion ceases, it is not averaged over different states of motion.

Periods of rest being short compared to the irradiation time period can as well result in increased dose errors. Therefore it is possible to base these on estimates or approximations of the motion cycle prior to a cease in motion. Even more preferable is to already stop the irradiation if the motion ceases for more than 30%, or respectively, 20% or even 10% of the motion cycle. It is advantageous thereby if the scans are distributed over the course of several or even many cycles.

A de-synchronization of the sequence of the irradiation from the cyclical motion can also be obtained when the beam approaching the matrix points does not "see" the cyclical motion of the target region at all. With a cyclical motion having resting periods, or respectively, with slowly traversing reversal points it is possible for the irradiation to take place during these time periods. The overall cyclically moved target region virtually does not move during these time periods. This results in a reduction of the interaction between the multiple irradiations and the motion and additionally in a limitation of the motion during the irradiation.

It is correspondingly preferred that the cyclical motion is monitored and a scan is only initiated when the motion has ceased.

It is furthermore preferred that the cyclical motion is monitored and its course is projected. It is then possible to initiate a scan only within a resting period, if the projection anticipates, such that the scan is at least 80%, better, entirely, completed during the resting period. This is particularly advantageous with volumetric procedures (see below).

In a preferred embodiment of the invention, the sequence of approaching the matrix points within the target matrix, which is the pathway, is modified from one scanning to another. Preferably the pathway is modified from one scanning to another. This is preferable both for two-dimensional as well as three-dimensional target regions as well as both for layered as well as volumetric procedures. Even when synchronization between the motion and the initiation of the scans occurs, different areas receive local dose errors which in turn cancel each other out, or respectively, are compensated for.

If it is possible to influence the cyclical motion, as may be the case, for example, with the breathing motion of a person, then it is possible to obtain de-synchronization through influencing the cyclical motion. For example, the duration of the cycle can be regularly or randomly modified or the cyclical motion at certain time periods, may cease, or respectively, begin at selected, somewhat evenly distributed or random points in time.

Preferably, during irradiation information regarding the cyclical motion is provided by means of a communication device. This information may be used to influence the cyclical motion as stated above. For example, a person may be requested to alter their breathing cycle at regular or randomly distributed intervals. Audio-visual feedback is particularly suited for this.

The irradiation, including all scans, may be arranged such that the intended dose is obtained for a specified motion sequence. With the aid of the communication device, this specific motion sequence can also be prescribed.

Furthermore, it is preferable that at least a portion of the scans are initiated with a random time delay, after the respective preceding scan. Preferably each of the scans is initiated after a time delay of a random interval. Random time delays of this type may also result in de-synchronization because the scans are not repeated with identical time separation, or periodically. The development of synchronization is thereby avoided accordingly. Exactly identical random time delays in relation to the motion are improbable. Ideally the random time delays are selected such that the scans are distributed over an, if applicable, variable time period. As an example, this time period can correspond to 50%, better 100% or even 150% of the duration of the cycle, such that, for example, at 100% it is ensured that a scan has taken place during all phases of the motion. However a distribution over at least two cycles or another, longer time period which may be selected may be useful.

The process may, as already mentioned above, be used with a three-dimensional target region, a target volume, to particular advantage as well. The intended dose distribution is then in terms of a spatial distribution; the target matrix is then also arranged in three-dimensions. As is already stated above, particle beams are particularly advantageous for three-dimensional target regions.

With a preferred embodiment, a first partial volume of the target volume is irradiated in more scans than a second partial volume. Advantageously, more than two partial volumes are irradiated, in each case with different numbers of scans. The approaching of individual matrix points with different numbers of scans, e.g., from one matrix point to another, may also be advantageous; for this, the matrix points may also be within one layer, or respectively, within one partial volume.

In this manner, partial volumes, layers or matrix points which exhibit a greater degree of motion may be irradiated with a greater number of scans than those that exhibit a lesser degree of motion; for this it is sufficient, if applicable, to execute a single scan for the application of the intended dose, in particular if said are at rest. The irradiation can, in this manner, be carried out more quickly.

Furthermore, due to the so-called pre-irradiation (see below) it may be useful to irradiate distal partial volumes, or respectively, layers or matrix points with more scans than proximal partial volumes. For this reason, a distribution in which the partial volume/layer/matrix points are irradiated from the distal regions to the proximal regions with successively fewer scans may be useful. In other words, one may also speak of an asymmetrical number of scans.

A target volume, or respectively the associated three-dimensional target matrix is frequently irradiated in layers. It is advantageous here for the initiation of the irradiation of at least a portion of the layers in a scan to be carried out after a random time delay. It is even better to carry out the initiation of the irradiation for all of the layers within a scan after random time delay; ideally this procedure is carried out in all scannings. In this manner an unfavorable synchronization between the scans in consecutive layers of the volume is less likely.

The random time delays between the initiations of the irradiation of individual layers contribute to the de-synchronization of the sequence of the irradiation from the cyclical motion on the whole. On the one hand, each delay corresponds to a phase difference in relation to the cyclical motion, in such a manner that a compensation for the influence of the layers to the deposited dose throughout the phases of the motion is supported. In addition, the scans take different lengths of time in a random manner, which also contributes to de-synchronization in basically the same manner as the random time delays between scans. The same exact random time delays with motion are extremely improbable.

Given a target volume and a three-dimensional target matrix that is scanned in layers, it is also preferable to modify the pathway in a layer from one scan to another; it is more preferable to modify the pathway in a layer for each scan. In this manner, the occurrence of a local dose error is made more difficult, because matrix points in a layer are approached at different points in time in relation to the initiation point in time of the respective scan.

It is also preferable that the pathway is modified from a first layer to a second layer. More preferably, the pathway is modified from one layer to the next; ideally it is modified with each layer change. Even if a synchronization between motion and scanning for each layer occurs, other interaction patters also occur which lead to an averaging.

If the target volume is not scanned in layers, but rather a pathway running through a volume (volumetric rescanning, or depth scanning), then it is equally preferable that the pathway be modified from one scanning to another.

In particular with these volumetric rescannings it is preferred that different partial volumes are irradiated with different numbers of scans.

A de-synchronization in accordance with the invention can also be obtained through modulation of the beam velocity, which is achieved advantageously through modulation of the beam intensity. Higher beam intensity allows for a correspondingly higher beam velocity to be selected. By varying the beam velocity decelerations and accelerations are integrated in the irradiation of the layers, or respectively, in the sequence of the scans, which basically have the exact same effect as a variation in the initiation point in time for layers, or respectively, scans. A modification of the motion parameters synchronized with intensity modification is extremely improbable, and thus in turn an averaging of the dose error is obtained.

The cycle, as presented above, can also be determined and, where applicable, projected, in order to set by adjusting the beam intensity, such that the scans are distributed over one of the time periods specified above.

The intensity of the beam can be modified during an extraction from an accelerator, such as a synchrotron or a cyclotron. Preferably this intensity modification is coordinated with the other irradiation parameters; in this manner it is possible to avoid deviating from the dose which is to be depositioned at the matrix points. It is however also possible to use a random modulation of the beam intensity for influencing the velocity with which the matrix points are approached.

The scanning rate (depth scanning or volumetric scanning) can be adjusted in the depth by means of an absorber pair or a modulator wheel.

Regarding the modulation of the beam intensity, an application can extend over the course of numerous cycles, in particular, the scannings can be distributed over numerous cycles.

As a rule, a target volume can be irradiated both in layers and volumetrically, e.g., consecutively, in an alternating manner or in combination. As an example, the target volume can first be irradiated volumetrically a number of times and then a number of times in layers.

With all of the embodiments of the invention, the irradiation can be distributed over numerous sessions (also known as so-called fractioned irradiation); for this, the total desired dose distribution is not obtained within a single session, but rather, it should be obtained only after completion of all of the sessions. An averaging of the dose errors is obtained over the course of numerous sessions. In particular, the structure of the multiple irradiations can be modified from one session to another; one scanning of a multiple irradiation, in an extreme case, corresponds to a single irradiation during a session. Particularly preferred is the application of the process to one single, in particular for each individual, session in which, during said individual session, a multiple irradiation is carried out, which means at least a portion of the points are irradiated numerous times.

The invention further concerns an irradiation apparatus for the deposition of an intended dose distribution to a cyclically moved target region, by means of multiple irradiations using a beam generating device and a control device whereby the beam generating device and the control device are designed to approach matrix points in a target matrix points in a target matrix with a beam in at least two scannings, whereby in each scanning, matrix points are irradiated sequentially. The irradiation apparatus is characterized in that it contains an evaluation unit, through which the maximal tolerance level for local deviation from the intended dose distribution is determined, that the control device is designed to de-synchronize the sequence of the irradiation and the cyclical motion of the target region and that it allows for a partitioning of the irradiations to the target region in a sufficient number of scannings such that local deviations from the intended dose distribution at most correspond to the maximal tolerance level for deviation from the target dosage distribution.

The beam generating device may be comprised of an accelerator, in particular a synchrotron or a cyclotron. The control device is designed to determine the sequence of the treatment and can function as an evaluation unit. It may be comprised of an appropriately programmed computer having the means, controlled by the computer, for influencing the beam spatially and the means for measuring the beam intensity. The computer may contain the evaluation unit in the manner that the programming of the computer contains the maximal tolerance level for the deviation from the intended dose distribution, in particular, said is explicitly integrated, or encoded in said.

The irradiation device is also designed to execute the process in accordance with the invention in all of its preferred embodiments.

Furthermore, the invention relates to a process for determining the control parameters for the above irradiation apparatus for executing the process for deposition of an intended dose distribution in a cyclically moved target region, in all preferred embodiments as well, by means of multiple irradiation with a beam approaching matrix points in a target matrix in at least two scannings, whereby in each of the scannings the matrix points are approached sequentially. Said parameter determination process is characterized by the steps: determining the maximal tolerance level for local deviations from the intended dose distribution, determining the procedure to be used for the de-synchronization of the irradiation sequence and the cyclical motion of the target region, and determining the distribution of the irradiation to the target region in a sufficient number of scannings such that local deviations from the intended dose distribution correspond to the maximal tolerance level for a deviation from the intended dose distribution. A "determination" comprises, in particular, the "defining" as well, such that the maximal tolerance level of deviation from the target dosage distribution may be defined.

The maximal tolerance level of local deviation from the intended dose distribution can basically be determined empirically; it is based, in particular, on the characteristics of the target which is to be irradiated, the intended doses distribution and the intended success of the treatment. The determination of the procedure to be used for de-synchronization as one of the parameters characterizing the irradiation is equal to, in the simplest case, the selection of the measures given above, which result in de-synchronization. The determination of the distribution in a sufficient number of scannings can either be carried out empirically or based on model calculations.

The preceding and following description of the individual characteristics relates to the device category as well as the process category, without the need for these to be individually stated explicitly in each case; the individual characteristics revealed thereby may also relate to the invention in manners other than those in the configurations shown.

In the following the invention shall be explained in greater detail based on embodiment examples.

The irradiation apparatus is designed to irradiate a target volume 102. The target volume 102 consists of a tumor near to, or within the lungs of a person. Alternatively it may also be a phantom, consisting of water or Plexiglas or some other material. The target volume moves in a cyclical manner upwards and downwards, indicated in FIG. 1 by the arrows above and below the target volume 102.

Figure 1:
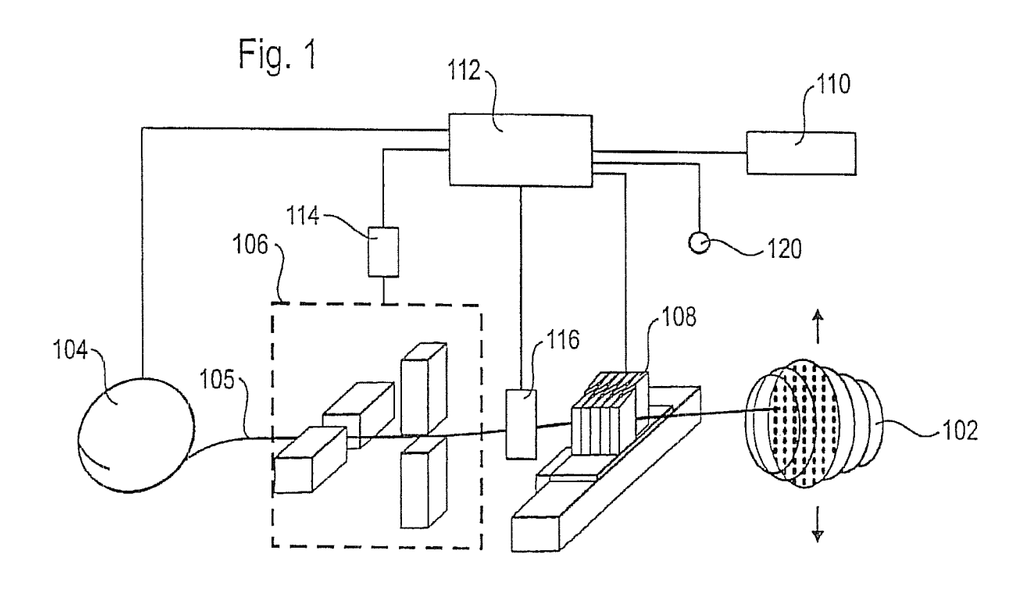
FIG. 1 shows a schematic illustration of an irradiation apparatus according to the invention for executing the process according to the invention.

The irradiation apparatus contains a synchrotron, a cyclotron or some other accelerator 104 for generating a particle beam 105, consisting of, for example, protons or $^{12}C$ nuclei. A beam of this type typically has an expansion of one or more millimeters, for example, in the range of 6 mm-10 mm. Layers are indicated in the target volume 102 which correspond to the depth of the Bragg peak for a specific particle energy (isoenergetic layers).

The irradiation apparatus directs a particle beam 105 to a matrix point in the target volume 102 at the points schematically indicated by black dots. Due to the simplified illustration, the approaching of matrix points layer by layer is shown; alternatively the matrix points can naturally also be approached in a volumetric manner (not shown).

A lateral influence to the particle beam 105 can be obtained by means of scanning magnets 106. In this case dipole magnets 106 are shown. For a longitudinal (along the beam direction) influence, the irradiation apparatus has a passive energy variation device in the form of a wedge-type system 108 for the modulation of energy. The wedge-type system 108 comprises wedges which are for instance made from plastics, which can be moved by a linear motor (not shown). The wedge-type system 108 is preferably used for volumetric scans. If the scans are executed in layers, the energy is preferably modified with the accelerator or an energy modulation unit installed upstream of the scanning magnets 105.

Furthermore the irradiation apparatus contains a detection device 110, a control device 112, a raster scanner 114 and a particle counter 116. The detection device 110 is designed to detect a motion in the target volume 102; for this it contains a detector system for recording the motion of the target region itself or alternatively, another movement correlated to this, such as a camera for detecting the motion of the chest surface.

The detection device 110 feeds the data collected regarding the motion of the target volume 102 to the control device 112.

The particle counter 116 determines the number of particles in the particle beam 105 and feeds this result as well to the control device 112.

The particle counter 116 may be, for example, an ionization chamber. The control device 112 which also functions as a controller is designed for controlling the accelerator 104, the scanner magnets 106 and the wedge-type system 108. For this, the control device 112 determines the appropriate control parameters taking into account the data received from the detection device 110 and from the particle counter 116.

Information for the person to be irradiated can be communicated through one of the communication devices 120 controlled by the control device 112. The communication device 120 can deliver audio or visual signals; it may be comprised of an LCD screen and a voice output.

The irradiation apparatus is used in accordance with the invention to deposit a specific dose with a specific distribution to the target volume 102. For this, the irradiation is subdivided into numerous scannings, whereby in each scanning the matrix points are approached partially or entirely in sequence. The number of scans is selected such that a determined deviation from the intended dosage distribution, basically 1.5%, is not exceeded.

In order to compensate at least in part for dose errors in the scans, according to the invention one or more parameters relevant to the irradiation treatment, depending on the characteristics of the cyclical motion, are modified during the irradiation treatment.

These concern, for example, the number of scannings, the beam intensity and thereby, normally interrelated, the rate at which the matrix points are approached, the temporal distribution of the scans, for instance based on the initiation point in time of the respective scan, the temporal distribution of the irradiation of layers, or respectively, of determined volumes within the individual scans, e.g., based on the initiation point in time of the irradiation of a layer, or respectively, a volume—either through modulated accelerator extraction or through passive energy modulation—, the selection of the initiation phase and/or the duration of the cycle, or respectively, an assumed duration of the cycle for this purpose and the pathway of the beam in the target volume 102, in particular within layers or volumes, respectively, within the target volume 102.

Figure 2:
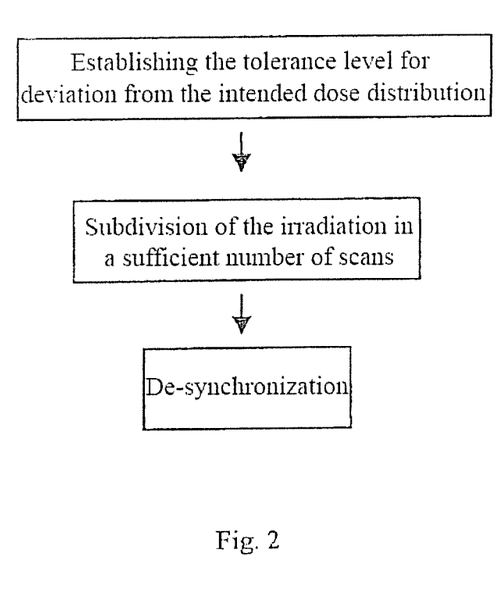
FIG. 2 shows a flowchart of the process according to the invention for deposition of an intended dose distribution.

The main features of the process listed above are shown in the flowchart presented in FIG. 2.

Characteristics of the multiple irradiations may depend on characteristics of the cyclical motion. For this, a characteristic of the cyclical motion is translated into a signal and transmitted to the control device 112 for controlling the multiple irradiations.

If the cyclical moved target is, for example, a tumor which moves due to the breathing process of a person, then the rising and lowering of the persons rib cage can be detected by the detection device 110, and the average breathing cycle, and if applicable, average amplitude can be determined and fed to the control device 112 for controlling the multiple irradiations. It is also possible to measure the motion of the target region directly, e.g. by means of X-ray images recorded continuously, or respectively, periodically, or through similar processes which are able to detect internal motions.

One or more of the following parameters of the multiple irradiation, as an example, can be adjusted for the cyclical motion in order to avoid exceeding the desired deviation from the intended dose distribution:
  the number of scans in a session;
  the beam intensity during a scan;

the velocity at which the beam moves from one matrix point to another within a scan;

the initiation point in time of the individual scans.

The concrete measures for de-synchronization depends, among other factors, on the target to be irradiated and can be determined on either an empirical basis or on the basis of model calculations.

The initiation points in time of the individual scans can be distributed over a section of the cyclical motion, over a cycle or over a time period which is longer than the duration of one cycle. The initiation points in time thereby can occur sequentially at regular intervals or be distributed randomly.

The signal for a characteristic of the cyclical motion can be determined basically within the framework of a planning phase prior to the actual irradiation. In this manner, a typical characteristic which is, respectively, object specific or person specific for the cyclical motion is determined in advance. The signal which is to be fed to the control device 112 can also be determined, if necessary additionally, numerous times, or respectively, continuously even during the irradiation procedure (online).

If a characteristic of the cyclical motion is determined prior to the actual irradiation procedure, it is possible to adjust for an average or typical motion cycle. If the motion cycle is known, then it is possible to adjust the irradiation parameters accordingly, and then the initiation points in time of the scans can be distributed either at regular intervals or randomly; or the scanning rate can be adjusted such that the scans are distributed over the course of the time period explicitly specified, once again, below. In order to avoid having to make an adjustment of the irradiation parameters during the irradiation procedure, it is convenient if the motion cycle remains consistent over the course of the irradiation procedure. As an example, it is possible to coach a person in advance to be able to maintain their breathing cycle at a comparatively constant rate (breath coaching).

The motion can be detected during the irradiation procedure however with the detection device 110 shown in FIG. 1, and by this means checked either a number of times or continuously.

In this manner, the actual motion cycle, or respectively, the phase of the motion as well, can be determined, and then communicated to the control device 112. A determination of the phase is, for example, easy to achieve with a person by the rising and lowering of the rib cage. By using the detection of the motion cycle, or respectively, phase of the motion it is possible to initiate the individual scans intentionally at different phases of the motion.

By use of the communication device 120 a person who is to be treated can be given an instruction signal at which point said person is to modify their breathing cycle at specific points in time or at random points in time during the irradiation procedure. For this, the person is given a command a points in time distributed at regular intervals over the irradiation period to modify their breathing motion by means of the communication device 120. The signals can be of an acoustic and/or optical nature.

It shall be emphasized once again that in addition to or alternatively to one of the structures of the irradiation procedure dependent on a characteristic of the cyclical motion, a characteristic of the irradiation can also be modified during the irradiation treatment. This too can be carried out at regular intervals or at randomly distributed points in time.

In this manner it is basically possible to modify the above specified parameters during a session. Furthermore, breaks between individual scans or the pathway of the beam can be modified during a session. In this example one or more parameters are modified from one scan to another. Alternatively, or in addition, the parameters are modified from one session to another.

With a structure for the irradiation procedure according to the invention the irradiation procedure is subdivided into numerous scans and the scans are distributed over the course of the cyclical motion such that the scans are applied in different phases of the cyclical motion. For this the initiation points in time can also be chosen in sequence at regular intervals, or random time delays between the scans can be introduced. The scans can be distributed over a typical or average motion cycle or a time period which is longer than one motion cycle, such as 150% of the motion cycle. Alternatively it is also possible to select a total irradiation period which lasts as long as two motion cycles or three motion cycles or a period which is longer than that of a single cycle.

Five, or better yet, 15-20 or as many as 30 scans can be selected. Typically, the target volume is subdivided into 50 layers. Normally it takes 100 ms up to 1 s to irradiate a layer. If a volume is irradiated, the duration of the approaching is normally measured in seconds.

The number of scans for different isoenergy layers or other partial volumes may also be chosen to differ. For this reason it makes sense to scan proximal layers less often than distal layers because in irradiating the distal layers, the proximal layers are also irradiated (one also speaks in this case of "pre-irradiating" the proximal layers).

If a section of the target region moves more quickly than another section, then the corresponding partial volumes may receive more scans than the slower moving partial volumes.

Furthermore, the irradiation can be halted when a resting of the cyclical motion has been detected by the detection device 110. If the motion ceases for more than 10% of the determined motion cycle, for example, then the irradiation is interrupted. In addition, the cycle can be projected; if the measured and the projected cycles do not coincide sufficiently, having a deviation, for example, of more than 10%, it is then advantageous to interrupt the irradiation.

Alternatively, a break in the cyclical motion can also be used to irradiate the target volume 102 during a resting phase. For this the motion is monitored by means of the detection device 110, and the continuation of the motion is projected by a computer in the detection device 110 or the control device 112 (based on an evaluation of the preceding cycles; using for instance extrapolation methods). If the prognosis indicates that it is possible to execute the irradiation during the resting phase, then it will be initiated. In regard to this scan, a nearly immobile target volume 102 is irradiated.

Figure 3:
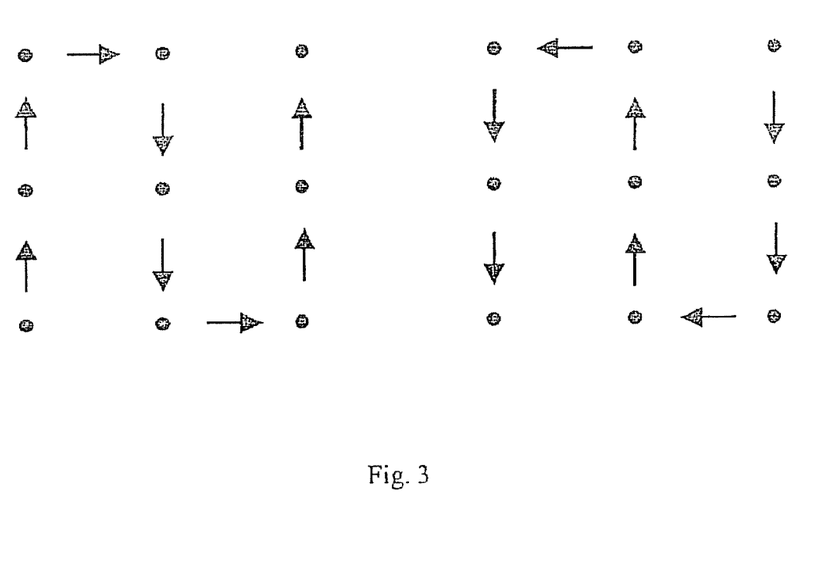
FIG. 3 shows a schematic diagram of a pathway of a beam approaching numerous matrix points.

The beam irradiating the target volume 102 may have a three-dimensional (volumetric) pathway, or can approach the target volume 102 in layers. In both cases the pathway can be modified from one scan to the next. If irradiation is carried out in layers, the sequence of the matrix points in one layer or in all layers can be modified from one scan to another. FIG. 3 illustrates schematically two single pathways in the same (isoenergetic) layer for two different scans. The arrows indicate thereby the sequence for irradiation of the matrix points. In the left image the pathway travels from the lower left corner to the upper right corner and in the right image from the right upper corner to the lower left corner.

If the target volume 102 is scanned in layers, then the initiation points in time for irradiation of the individual layers may be selected to be distributed randomly, or respectively, time delays of random periods between the irradiation of the individual layers may be introduced. In particular, the time delays may be selected such that as a whole one of the above specified time periods for a session of multiple irradiations results. In addition, from one layer to another, even within the same scan, a different pathway may be selected.

Independently of whether the target volume 102 is scanned in layers or volumetrically, the scanning rate can be modulated by modulating the beam intensity. For this, the intensity of the beam is defined during the extraction from the accelerator, which means it is adjusted for the other irradiation parameters—including the number of particles to be deposited per matrix point—can be modified. The intensity modulation can, for example, be random. For this the intensity of the beam is adjusted such that the irradiation takes place over the course of the specified time interval.

The rate of the depth modulation (depth scanning in volumetric rescanning) can be modified by means of the wedge-shaped absorber pair 108 or by means of a modulator wheel (not shown) with a specific sequence or with a random sequence.

Figure 4:
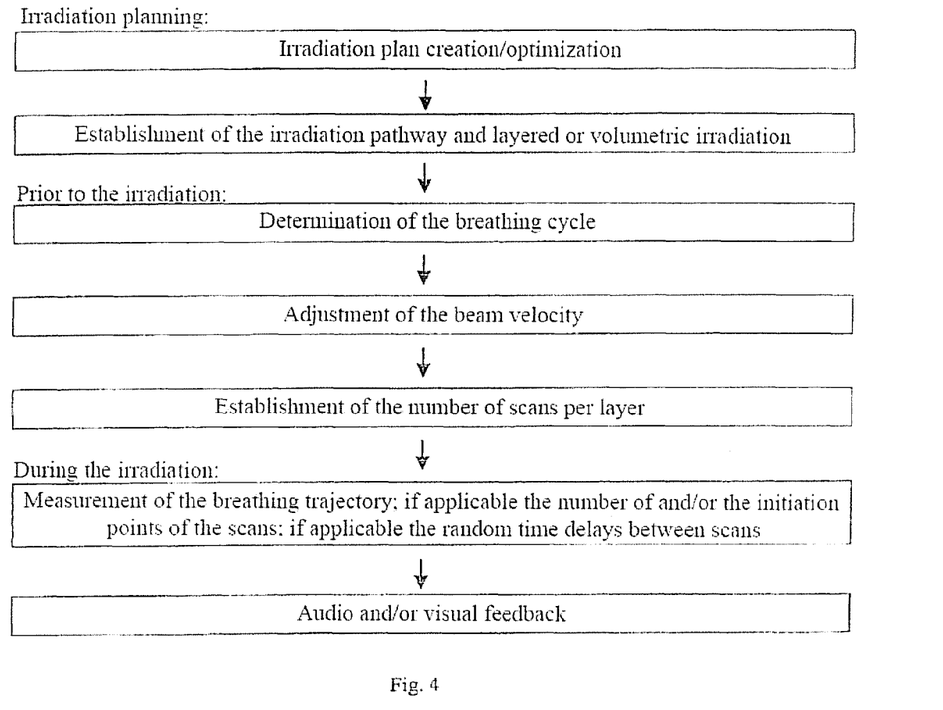
FIG. 4 shows a second flowchart of the process according to the invention for deposition of an intended dose distribution.

FIG. 4 shows an exemplary sequence of the irradiation process according to the invention for the treatment of a human being whereby the cyclical motion of the target is caused by the breathing of the subject. For this an irradiation plan is made in advance consisting of the adjustment, or respectively, the optimization of the irradiation plan, the determination of whether the irradiation should be carried out in layers or volumetrically and the corresponding determination of the irradiation pathway. An irradiation pathway can also be determined first and then it can be determined whether the irradiation is to be carried out in layers or volumetrically. In the framework of the planning of the treatment other parameters determining the irradiation can be established regarding the, where applicable, random initiations of the scans per layer, the time delays between scans or whether feedback is given to the person being treated. Prior to the, or respectively, prior to each, irradiation treatment, the breathing cycle is determined, the beam velocity is adjusted and thereby the rate at which the matrix points are approached, and the number of scans per layer is established. During the treatment, the breathing trajectory is measured and if applicable, used to adjust the number of scans, or respectively, the initiation points in time of the scans. Where applicable, the time delays between scans can also be randomly selected. The person being treated receives audio and/or visual feedback regarding the measured trajectory and/or regarding the intended trajectory.

The irradiation procedure according to the invention can also be executed, distributed over the course of numerous sessions (so-called fractions). The intended dose distribution is based then on the radiation to be applied as a whole in all of the sessions combined. The averaging of the fractions can contribute to the de-synchronization. The sequence of the irradiations in particular may be selected such that it is different from one session to another.

Figure 5:
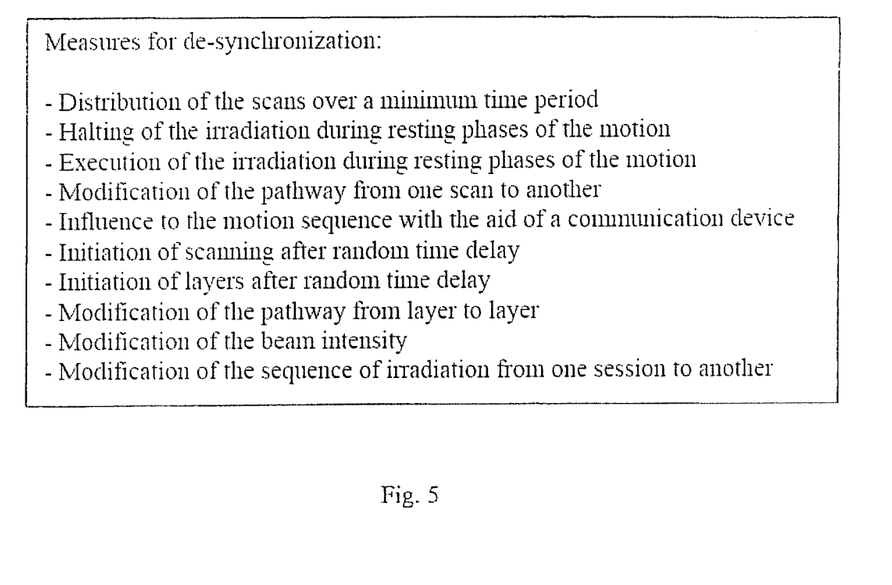
FIG. 5 shows a selection of the measures for de-synchronization.

FIG. 5 shows a selection of the already specified de-synchronization measures in an overview.

Figure 6:
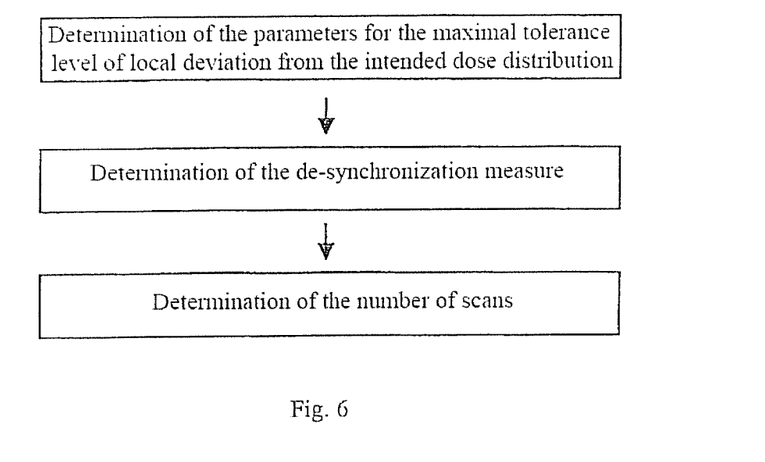
FIG. 6 shows a flowchart of the process according to the invention for determining control parameters.

FIG. 6 shows a flowchart of the process for determining the control parameters of the irradiation apparatus. It comprises the steps: determination of parameters for the maximal tolerance level of local deviations from the intended dose distribution, determination of the procedural method for de-synchronization of the sequence of the irradiation and the cyclical motion of the target region (102), and determination of the partitioning of the irradiation treatment to the target region in a sufficient number of scans, such that local deviations from the intended dose distribution at most correspond to the maximal tolerance level of deviation from the target dosage distribution. As already indicated above, it is possible to determine these parameters either empirically or on the basis of model calculations.

What is claimed:

1. A process for the deposition of an intended dose distribution in a cyclically moved target region by means of multiple irradiations with a beam irradiating matrix points of a target matrix in at least two scans by which in each of the scans matrix points are approached sequentially, characterized by the steps:
    establishing a maximal tolerance level for local deviation from the intended dose distribution,
    de-synchronizing the sequence of the irradiation and the cyclical motion of the target region, and
    partitioning the irradiation of the target region in a sufficient number of scans such that local deviations from the intended dose distribution due to movement of the cyclically moved target region at most correspond to the maximal tolerance level for local deviation from the intended dose distribution, wherein the motion is monitored and the irradiation is halted when the motion ceases for more than 50% of the cyclical motion.

2. A process for the deposition of an intended dose distribution in a cyclically moved target region by means of multiple irradiations with a beam irradiating matrix points of a target matrix in at least two scans by which in each of the scans matrix points are approached sequentially, characterized by the steps:
    establishing a maximal tolerance level for local deviation from the intended dose distribution,
    de-synchronizing the sequence of the irradiation and the cyclical motion of the target region, and
    partitioning the irradiation of the target region in a sufficient number of scans such that local deviations from the intended dose distribution due to movement of the cyclically moved target region at most correspond to the maximal tolerance level for local deviation from the intended dose distribution,
    wherein the cyclical motion is monitored and wherein the sequence of the cyclical motion is also projected and wherein a scanning is initiated only during a resting phase of the motion when the monitoring indicates that the scanning will be at least 80% completed during the resting phase.

3. A process for the deposition of an intended dose distribution in a cyclically moved target region by means of multiple irradiations with a beam irradiating matrix points of a target matrix in at least two scans by which in each of the scans matrix points are approached sequentially, characterized by the steps:
    establishing a maximal tolerance level for local deviation from the intended dose distribution,
    de-synchronizing the sequence of the irradiation and the cyclical motion of the target region, and
    partitioning the irradiation of the target region in a sufficient number of scans such that local deviations from the intended dose distribution at most correspond to the maximal tolerance level for local deviation from the intended dose distribution,
    wherein the initiation of at least a portion of the scans occurs after a time delay of a random period.

4. The process according to claim 1, 2, or 3, wherein a characteristic of the multiple irradiations is dependent on a characteristic of the cyclical motion.

5. The process according to claim 1, 2, or 3, wherein a characteristic of the multiple irradiations is modified during the multiple irradiations.

6. The process according to claim 5, wherein a characteristic of the multiple irradiations is modified randomly during the multiple irradiations.

7. The process according to claim 1, 2, or 3, wherein at least a portion of the matrix points is approached in different phases of the cyclical motion.

8. The process according to claim 7, wherein the cyclical motion is monitored.

9. The process according to claim 1, 2, or 3, wherein the cyclical motion is determined and at least a portion of the scans is distributed over a time period which corresponds to at least 50% of the cyclical motion.

10. The process according to claim 9, wherein the cyclical motion is determined prior to the irradiation treatment.

11. The process according to claim 9, wherein the cyclical motion is determined numerous times through monitoring the motion during the irradiation.

12. The process according to claim 1 or 3, wherein the cyclical motion is monitored and wherein a scanning is initiated only during a resting phase of the motion.

13. The process according to claim 1, 2, or 3, wherein the sequence of the approaching of the matrix points is modified from one scanning to another.

14. The process according to claim 1, 2, or 3, wherein information pertaining to the cyclical motion is provided by means of a communication device.

15. The process according to claim 1, 2, or 3, wherein the target region is a target volume and the intended dose distribution and the target matrix are three-dimensional.

16. The process according to claim 1, 2, or 3, wherein the beam velocity is modulated by means of modulating the intensity of the beam.

17. The process according to claim 1, 2, or 3, wherein the multiple irradiation is distributed over numerous sessions and is structured differently from one session to another.

18. A process for the deposition of an intended dose distribution in a cyclically moved target region by means of multiple irradiations with a beam irradiating matrix points of a target matrix in at least two scans by which in each of the scans matrix points are approached sequentially, characterized by the steps:
establishing a maximal tolerance level for local deviation from the intended dose distribution,
de-synchronizing the sequence of the irradiation and the cyclical motion of the target region, and
partitioning the irradiation of the target region in a sufficient number of scans such that local deviations from the intended dose distribution at most correspond to the maximal tolerance level for local deviation from the intended dose distribution,
wherein the target region is a target volume and the intended dose distribution and the target matrix are three-dimensional, and wherein the three-dimensional target matrix is scanned in layers and wherein the initiation of the irradiation for at least a portion of the layers in one of the scannings occurs with a random time delay.

19. The process according to claim 18, wherein a first partial volume of the target volume is irradiated in more scans than a second partial volume.

20. The process according to claim 18, wherein the number of scans for at least a portion of the matrix points varies.

21. The process according to claim 18, wherein the three-dimensional target matrix is scanned in layers and the number of scans for at least a portion of the layers varies.

22. The process according to claim 18, wherein the three-dimensional target matrix is scanned in layers and wherein a pathway in a layer is modified from one scanning to another.

23. The process according to claim 18, wherein the three-dimensional target matrix is scanned in layers and wherein the pathway is modified from a first layer to a second layer within the same scanning.

24. The process according to claim 18, wherein the beam approaches a pathway through a volume and the pathway is modified from one scanning to another.

25. An irradiation apparatus for the deposition of an intended dose to a cyclically moved target region by means of multiple irradiations having a beam generating device and a control device, wherein the beam generating device and the control device are designed for approaching matrix points of a target matrix with a beam in a least two scannings, wherein in each of the scannings the matrix points are irradiated sequentially, characterized in that the irradiation apparatus has a defining unit through which a maximal tolerance level for deviation from the intended dose distribution is defined, that the control device is equipped for de-synchronization of the sequence of the irradiation and the cyclical motion of the target region and allows for a partitioning of the irradiation of the target region in a sufficient number of scannings in order that local deviations from the intended dose distribution due to movement of the cyclically moved target region correspond at most to the maximal tolerance level for deviation from the intended dose distribution, and wherein the irradiation apparatus is designed to randomly modify a characteristic of the multiple irradiations during the multiple irradiation.

26. The irradiation apparatus according to claim 25, designed to select a characteristic of the multiple irradiations in relation to a characteristic of the cyclical motion.

27. The irradiation apparatus according to claim 25, designed to irradiate a least a portion of the matrix points in different scannings in different phases of the cyclical motion.

28. The irradiation apparatus according to claim 25, designed to determine the cyclical motion and to distribute at least a portion of the scans over a time period which corresponds to at least 50% of the cyclical motion.

29. The irradiation apparatus according to claim 25, designed to modify the sequence of the approaching of the matrix points from one scanning to another.

30. The irradiation apparatus according to claim 25, designed such that the initiation of at least a portion of the scans can occur after a time delay of a random length.

31. The irradiation apparatus according to claim 25, designed such that for a target volume as the target region, the intended dose distribution and the target matrix are three-dimensional.

32. The irradiation apparatus according to claim 25, designed to monitor the motion and halt irradiation when the motion ceases for more than 50% of the cyclical motion.

* * * * *